United States Patent [19]

Shimizu et al.

[11] Patent Number: 5,705,635

[45] Date of Patent: Jan. 6, 1998

[54] METHOD FOR THE PREPARATION OF ULTRAFINE FIBROUS ASSEMBLY HAVING TWISTED MORPHOLOGY

[75] Inventors: Toshimi Shimizu, Tsukuba; Mitsutoshi Masuda, Matsudo, both of Japan

[73] Assignee: Japan as represented by Director General of Agency of Industrial Science and Technology, Tokyo-to, Japan

[21] Appl. No.: 752,437

[22] Filed: Nov. 14, 1996

[30] Foreign Application Priority Data

Nov. 20, 1995 [JP] Japan .................. 7-325031

[51] Int. Cl.⁶ .................. G07H 1/00; G07H 5/04
[52] U.S. Cl. .................. 536/124; 536/17.9; 536/55.2; 536/55.3
[58] Field of Search .................. 536/124, 17.9, 536/55.2, 55.3

[56] References Cited

U.S. PATENT DOCUMENTS 5,403,922  4/1995  Garelli-Calvet .................. 536/124

OTHER PUBLICATIONS

Goue'th et al, Carbohydrate Research, 266 (1995), pp. 171–189.
Lafont et al, Journal of Carbohydrate Chemistry, 14 (4 & 5), pp. 533–550 (1995).
F.M. Menger et al., *J. Am. Chem. Soc.*, 116, 5987–5988 (1984).
F.M. Menger et al., *Adv. Mater.*, 7(7), 669–671 (1995).

*Primary Examiner*—John Kight
*Assistant Examiner*—Everett White
*Attorney, Agent, or Firm*—Wenderoth, Lind & Ponack

[57] ABSTRACT

When a saturated aqueous solution of a bolaform glycolipid represented by the general formula

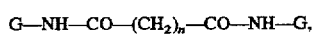

$$G-NH-CO-(CH_2)_n-CO-NH-G,$$

in which G is a residue derived from a D- or L-glucopyranose by excepting the reduced-terminal hydroxyl group and the subscript n is 10, 12 or 14, at a high temperature, e.g., 90 °C. or higher, is cooled at a controlled rate of 0.5 °C./minute or lower, crystallite growth of the precipitates proceeds to form an ultrafine fibrous assembly of up to several hundreds μm length having a twisted fibrous morphology of right- or left-hand screw. The twisted fibrous assembly thus obtained has usefulness as a functional material in the field of fine chemicals and in the fields of electronic and information technologies.

3 Claims, 2 Drawing Sheets

10 μm

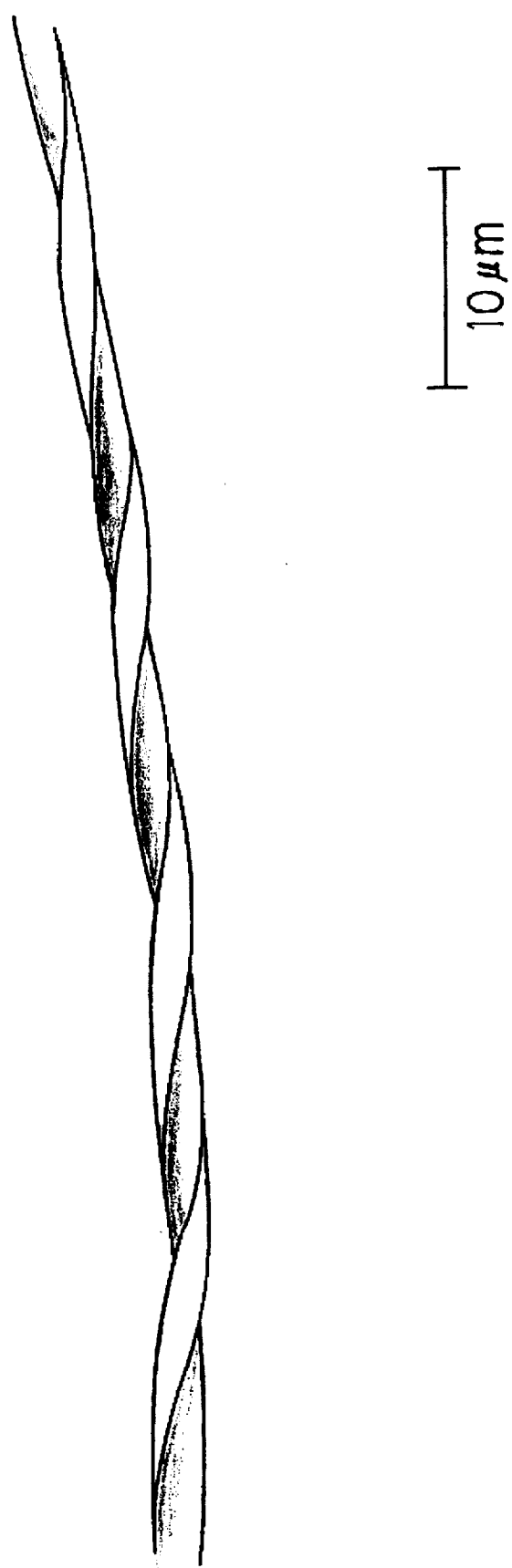

METHOD FOR THE PREPARATION OF ULTRAFINE FIBROUS ASSEMBLY HAVING TWISTED MORPHOLOGY

BACKGROUND OF THE INVENTION

The present invention relates to a method for the preparation of an ultrafine fibrous assembly having a twisted morphology consisting of self-assembling "bolaform" or two-headed glycolipid molecules having an optically active glucopyranosyl head group at each molecular end and having usefulness as a functional material in the fields of fine chemicals, information technology and so on.

It is known in the prior art that a lipid capable of forming a stable molecular aggregate by means of self-assembling has usefulness in various fields including the field of fine chemicals. Known methods for the preparation of such molecular aggregates consisting of the lipid molecules include those in which a spherical molecular aggregate called a liposome consisting of molecules of a naturally occurring phospholipid is prepared by the application of a thin-film method, thermal dispersion method, solution injection method, cholic acid method, reversed-phase evaporation method and the like (see "Experimental Method on Biomembranes", volume 2 by K. Inoue, edited by Akamatsu, et al., page 185, Kyoritsu Publishing Co., 1974). These prior art methods, however, are defective because, in addition to the complicacy of the process requiring high skillfulness, the molecular aggregates obtained by the method are limited to a spherical monolayered or multilayered vesicle only and no elongated fibrous aggregates can be obtained thereby.

On the other hand, it is also known that a long helically wound or rod-like fibrous molecular aggregate can be prepared by dispersing a synthetic amphiphilic compound in water (see Journal of American Chemical Society, volume 107, 1985, pages 509 to 510). This method, however, is not versatile because the molecular aggregate obtained by this method is stable only in water and the special morphology thereof is destroyed in air. Thus, the morphology thereof so that the applicability of the fibrous assembly as an ultrafine molecular aggregate is limited to several specific fields.

SUMMARY OF THE INVENTION

The present invention accordingly has an object to provide a novel and efficient method for the preparation of an ultrafine fibrous assembly having a twisted morphology and a length of several μm to several hundreds μm and highly stable even in air, which cannot be prepared by any prior art methods, starting from a natural phospholipid or conventional synthetic amphiphilic compound.

Thus, the method of the present invention for the preparation of an ultrafine fibrous assembly having a twisted morphology comprises the steps of:

(a) dissolving, in water, a "bolaform" (see Journal of the American Chemical Society, volume 108, 1986, page 1785) glycolipid represented by the general formula

in which G is a D- or L-glucopyranosyl group and the subscript n is a positive number of 10, 12 or 14, to form an aqueous solution which is heated at a temperature of 90° C. or higher; and (b) cooling the aqueous solution at a rate not exceeding 0.5° C. per minute down to a temperature not higher than 30° C. so as to effect growth of crystallites.

BRIEF DESCRIPTION OF THE DRAWING

FIG. 2 is a sketch from a polarized-light micrograph of the ultrafine fibrous assembly obtained in Example 2.

DETAILED DESCRIPTION OF THE PREFERRED EMBODIMENTS

Figure 1:
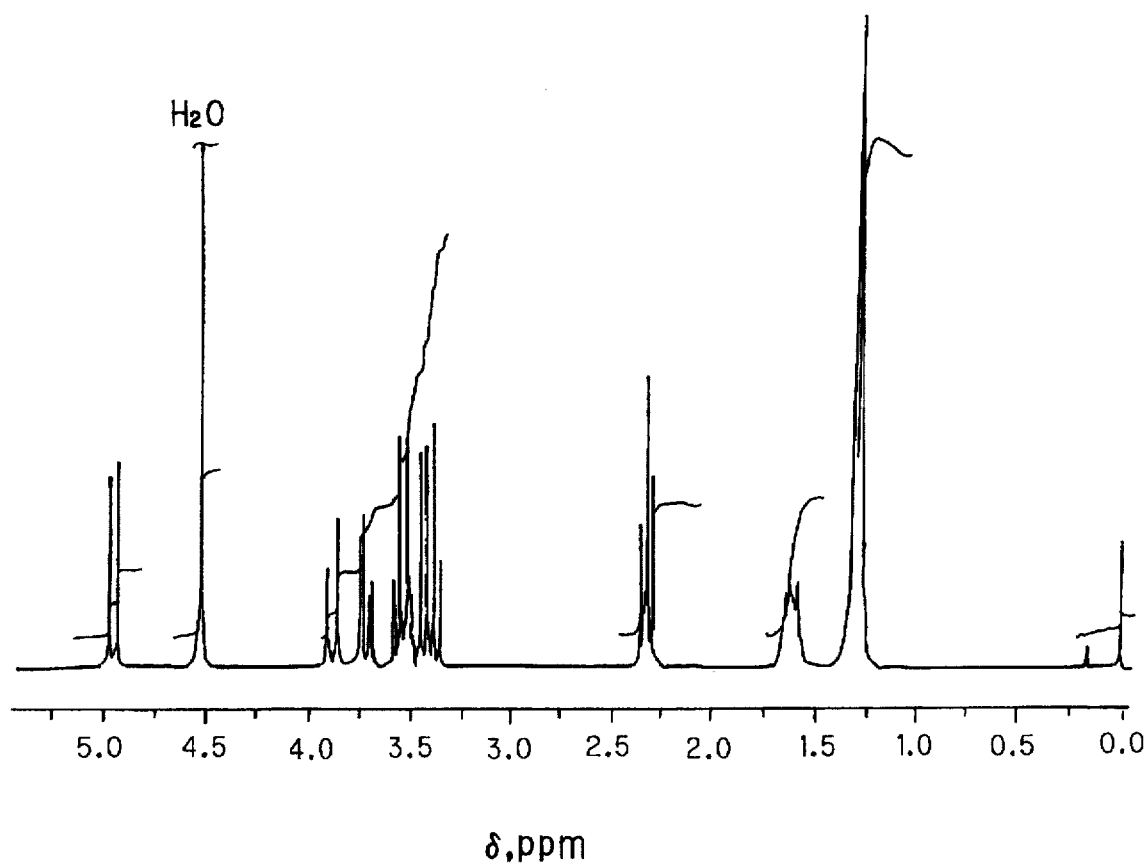
FIG. 1 is a $^1$H-NMR spectrum of N,N'-bis(β-D-glucopyranosyl) decane-1,10-dicarboxamide.

The above described method of the invention has been established as a result of the extensive investigations undertaken by the inventors with an object to develop an efficient method for the preparation of an ultrafine fibrous assembly having a twisted morphology and highly stable in air leading to a discovery that the desired fibrous assembly can be obtained by very slowly cooling a hot aqueous solution containing a bolaform glycolipid consisting of two optically active glucopyranosyl groups each connected via an amide linkage to the end of a long-chain alkylene group having a specific chain length to effect growth of crystallites forming a fibrous assembly.

The starting material for the ultrafine fibrous assembly used in the inventive method is a bolaform glycolipid represented by the above given general formula (I). The group denoted by G at each molecular end thereof must be optically active in order that the ultrafine fibrous assembly obtained by the method has a twisted morphology. Typically, the group G can be a D- or L-glucopyranosyl group which is a residue derived from D- or L-glucopyranose by excepting the reduced-terminal hydroxyl group and a residue connected to the N-glycoside linkage. While each of these glucopyranosyl groups has two anomeric isomerisms of α- and β-anomers since the carbon atom at the reduced terminal is asymmetric, the method of the present invention is applicable to both of these anomers.

It is a very unexpected discovery that the method of the invention is successful only when the subscript n in the above given general formula (I) of the starting compound is an even number of 10, 12 or 14. When the value of n is smaller than 10, the molecular aggregate to be formed has a morphology of a needle-like or platelet-formed crystal and no ultrafine fibrous assembly with a twisted morphology can be obtained. When the value of n is larger than 14, on the other hand, no fibrous assembly can be obtained and the resultant crystals are in the form of a small platelet although the crystals exhibit a twisted morphology. When the value of n is an odd number of 11 or 13, an ultrafine fibrous assembly cannot be obtained at all if not to mention of the twisted morphology of the fibrous assembly.

The above described bolaform glycolipid represented by the general formula (I) is a novel compound not described in any prior art literatures. This compound can readily be prepared by the method described below.

The starting material of the method is a D- or L-glucopyranosyl azide derivative represented by the general formula

in which acetylG is a group obtained by acetylating all of the hydroxyl groups in the above defined group G. This compound is a known compound described, for example, in Berichte der Deutschen Chemische Gesellschaft, volume 63, page 836 (1930).

In the first step, the azide compound of the general formula (II) as the starting material is subjected to hydrogenation in the presence of a catalyst such as platinum oxide to give D- or L-glucopyranosyl amine. In the next step, this amine derivative, which can be used without isolation and further purification, is subjected to a condensation reaction with an alkane dicarboxylic acid represented by the general formula

HO—CO—(CH$_2$)$_n$—CO—OH,  (III)

in which the subscript n has the same meaning as defined above, followed by deprotection of all of the acetyl groups on the glucoside residue to give the desired compound of the general formula (I). The above mentioned condensation reaction proceeds by coupling in the presence of a condensing reagent conventionally used in the peptide synthesis such as 1-ethyl-3-(3-dimethylaminopropyl) carbodiimide hydrochloride, 1-hydroxybenzotriazole and the like. Other condensing reagents usable here include diethyl phosphorocyanidate, isobutyl chloroformate and 1-ethoxycarbonyl-2-ethoxy-1,2-dihydroquinoline. Instead of the above mentioned alkane dicarboxylic acid, the coupling reaction of the amine derivative may be performed with a dicarboxylic acid dichloride. The compounds of the general formula (I) thus obtained are each a white solid at room temperature melting at 222°–225° C., 220°–224° C. and 227°–229° C. for the value of n of 10, 12 and 14, respectively.

In step (a) of the inventive method, the starting compound is added to and dissolved in distilled water in such a volume in the range from 5 ml to 2000 ml or, preferably, from 10 ml to 500 ml per g of the starting compound to give an aqueous solution which is desirably saturated with the solute at an elevated temperature. When the volume of water is too small, the solute added to the aqueous medium cannot be dissolved therein leaving an undissolved portion of the compound even by increasing the temperature to the boiling point of water. When the volume of water is too large, on the other hand, the concentration of the solute in the aqueous solution is too low, and thus does not reach the saturation concentration, so that no ultrafine fibrous assembly could be precipitated by the slow cooling of the aqueous solution. From the standpoint of obtaining an aqueous solution of the solute concentration as high as possible, it is important that the aqueous solution is kept at a temperature of 90° C. or higher.

In step (b) of the inventive method, the aqueous solution containing the starting compound and kept at a temperature of 90° C. or higher is cooled at a controlled rate not exceeding 0.5° C./minute or, preferably, not exceeding 0.1° C./minute down to room temperature or a temperature not higher than 30° C. It is important that the aqueous solution under cooling is kept standing still without any agitation. The cooling rate should be as low as possible from the standpoint of obtaining a well-defined ultrafine fibrous assembly although an excessively small cooling rate is accompanied by a disadvantage of decreased productivity as a matter of course. When the cooling rate of the aqueous solution is too large, an ultrafine fibrous assembly of a well-defined length can hardly be obtained but the precipitates formed in the aqueous medium are mostly in the form of a needle or rod.

The thus obtained ultrafine fibrous assembly has a twisted morphology of a right-handed or left-handed screw depending on D- or L-configuration of the group G in the starting compound. The twisted morphology of the ultrafine assembly can readily be recognized by using a transmission or scanning electron microscope, when the fiber diameter is relatively small, or by using a polarizing or phase-contrast microscope. When the conditions for the preparation are appropriately controlled, it is easy to obtain an ultrafine fibrous assembly of a twisted morphology having a diameter in the range from several tens of nm to several thousands of nm and a length from several μm to several hundreds of μm with a length:diameter ratio of 100 or larger. The ultrafine fibrous assembly prepared according to the inventive method and separated from the aqueous medium and dried by air-drying or by vacuum drying is very stable in air without any noticeable changes in the morphology for a period of one year or even longer provided that the storage conditions are adequate including the temperature which is not excessively high, exceeding, for example, 200° C.

The ultrafine fibrous assembly of a twisted morphology obtained by the above described inventive method, which can never be obtained from natural phospholipids or conventional synthetic amphiphilic compounds, has usefulness as a substrate of drug-delivery system or as an inclusion material in the fields of fine chemical industries for medicaments, dyes and cosmetic or toiletry compositions as well as in the fields of food industries, agricultural industries, fiber industries and the like as an emulsifying agent, stabilizer, dispersing agent or moisturizing agent. Further possibility of application of the ultrafine fibrous assembly of the invention is in the fields of electronic and information technologies to provide unique fine electronic devices by coating the fibrous assembly with a metal or an electroconductive material. In addition, the twisted morphology of the ultrafine fibrous assembly is suggestive of the application thereof to specific advanced optical devices and resolution agents for the resolution of a racemate into the component enantiomers.

In the following, the method of the present invention is described in more detail by way of examples, which, however, never limit the scope of the invention in any way. The Examples are preceded by a Reference Example describing the procedure for the preparation of the starting compound represented by the general formula (I) in which the value of the subscript n is 10.

In the thin-layer chromatography conducted in the Reference Example below, the $R_f$ value was determined by using either a 20:1 by volume mixture of chloroform and methyl alcohol or a 65:30:5 by volume mixture of chloroform, methyl alcohol and water as the developing solvent to record the results as $R_f1$ and $R_f2$, respectively.

REFERENCE EXAMPLE

Into a solution prepared by dissolving 5.0 g (12.2 mmoles) of 2,3,4,6-tetra-O-acetyl-β-D-glucopyranosyl bromide in 120 ml of dimethyl formamide were added, with stirring, 15.8 g (243 mmoles) of sodium azide and this reaction mixture was stirred for 24 hours at room temperature under shielding of light. Thereafter, the reaction mixture was added drop by drop into 1000 ml of ice water with stirring followed by extraction of the insoluble material with 900 ml of methylene chloride. The thus obtained organic solution was washed with ice water and dried over anhydrous sodium sulfate. After removal of the desiccant by filtration, the solution was subjected to evaporation of the solvent under reduced pressure to dryness to give a light yellow solid which was, after washing with diethyl ether and drying, recrystallized from isopropyl alcohol to give 3.30 g of white needle-like crystals having a $R_f1$ value of 0.4 in the thin-layer chromatography and a melting point of 131° to 132° C., which could be identified as 2,3,4,6-tetra-O-acetyl-β-D-glucopyranosyl azide from the result of the elementary analysis shown below. The above mentioned yield of this product was 79% of the theoretical value.

| Elementary analysis | C | H | N |
|---|---|---|---|
| calculated, %, as $C_{14}H_{19}O_9N_3$ | 45.04 | 5.13 | 11.26 |
| found, % | 45.36 | 5.10 | 11.14 |

Separately, 674 mg (2.9 mmoles) of 1,10-decane dicarboxylic acid admixed with a drop of dimethyl formamide and 1.05 ml (14.5 mmoles) of thionyl chloride were heated for 1 hour under reflux followed by removal of the unreacted thionyl chloride by evaporation under reduced pressure to give a light yellow liquid which was 1,10-decane dicarboxylic acid dichloride.

A reaction mixture prepared by dissolving 2.38 g (6.4 mmoles) of 2,3,4,6-tetra-O-acetyl-β-D-glucopyranosyl azide prepared as described above in 300 ml of methyl alcohol with addition of 1000 mg of platinum oxide under an atmosphere of nitrogen was stirred at room temperature for 2 hours under bubbling of hydrogen gas and the reaction mixture was filtered under suction by using Celite to give a filtrate which was concentrated by evaporation of the solvent under reduced pressure. The concentrated solution was dissolved in 30 ml of dimethyl formamide containing 0.77 ml of pyridine and 20 ml of a methylene chloride solution containing 781 mg (2.9 mmoles) of the 1,10-decane dicarboxylic acid dichloride prepared above were added dropwise to the dimethyl formamide solution of the concentrated filtrate with stirring at room temperature, followed by continued stirring for 24 hours. The reaction mixture was extracted with chloroform/water and the organic solution obtained by phase separation was washed first with a 5% by weight aqueous solution of citric acid and then with a 5% by weight aqueous solution of sodium hydrogencarbonate followed by drying over anhydrous sodium sulfate and removal of the solvent by evaporation under reduced pressure.

The thus obtained crude product was subjected to purification by the silica gel column chromatography with a 20:1 by volume mixture of chloroform and methyl alcohol as the eluent to give 1.50 g of a colorless and amorphous solid product, which was N,N'-bis(2,3,4,6-tetra-O-acetyl-β-D-glucopyranosyl) decane-1,10-dicarboxamide, in a yield of 56%. This product was dissolved in 30 ml of methyl alcohol to give a solution into which 0.6 ml of a 0.05 N methyl alcohol solution of sodium methoxide was added dropwise with stirring at room temperature to effect the reaction for 3 hours followed by neutralization of the mixture by the addition of a strongly acidic cation exchange resin and removal of the solvent by distillation.

Finally, the product was subjected to purification by the silica gel column chromatography with a 65:30:5 by volume mixture of chloroform, methyl alcohol and water as the eluent to give 878 mg of a white powder, which was N,N'-bis(β-D-glucopyranosyl) decane-1,10-dicarboxamide, in a yield of 95%.

The physical properties and the results of the elementary analysis of this product were as shown below.

Melting point: 222° C.

Specific rotation $[\alpha]_D$ : −16.8 (c=0.29, in water)

$R_f$ in thin-layer chromatography: $R_f2$=0.3

| Elementary analysis | C | H | N |
|---|---|---|---|
| calculated, %, as $C_{24}H_{44}O_{12}N_2 \cdot 3H_2O$ | 47.52 | 8.31 | 4.62 |
| found, % | 47.58 | 8.15 | 4.56 |

FIG. 1 of the accompanying drawing is a $^1$H-NMR spectrum of this compound (concentration 15 mg/0.6 ml, in deuterium oxide, 270 MHz).

EXAMPLE 1

A 100 mg (0.18 mmole) portion of the above obtained N,N'-bis(β-D-glucopyranosyl) decane-1,10-dicarboxamide taken in a flask was admixed with 7 ml of distilled water and dissolved therein by heating to boiling by using a mantle heater. Thereafter, the temperature of the aqueous solution was gradually decreased at a rate of 0.1° C. per minute down to a temperature of 30° C. with fine adjustment of the power supply to the heater and then the solution was kept standing as such at room temperature for 2 days so that fibrous assemblies were formed and precipitated in the solution. The supernatant was discarded by decantation and the fibrous assemblies were air-dried in open air. The thus obtained fibrous assemblies having a length of several hundreds of μm could be examined by the use of a polarized-light microscope to find that each fibrous assembly had an ultrafine fibrous morphology twisted in the direction of a right-hand screw.

EXAMPLE 2

The experimental procedure was substantially the same as in Example 1 excepting replacement of 100 mg of the N,N'-bis(β-D-glucopyranosyl) decane-1,10-dicarboxamide with the same amount (0.17 mmole) of N,N'-bis(β-D-glucopyranosyl) dodecane-1,12-dicarboxamide, which had been prepared in substantially the same manner as in the Reference Example described above excepting replacement of the 1,10-decane dicarboxylic acid dichloride with the same molar amount of 1,12-dodecane dicarboxylic acid dichloride, and increase of the volume of water, in which the N,N'-bis(β-D-glucopyranosyl) dodecane-1,12-dicarboxamide was dissolved, from 7 ml to 10 ml. Fibrous assemblies, having a length of several hundreds of μm, were obtained and examined by the use of a polarized-light microscope or phase-contrast light microscope easily to find that each fibrous assembly had an ultrafine fibrous morphology twisted in the direction of a right-hand screw. FIG. 2 of the accompanying drawing is a sketch from a polarized-light microscopic photograph of the fibrous assemblies showing the twisted morphology thereof.

EXAMPLE 3

The experimental procedure was substantially the same as in Example 2 excepting replacement of the N,N'-bis(β-D-glucopyranosyl) dodecane-1,12-dicarboxamide with the same amount of N,N'-bis(β-L-glucopyranosyl) dodecane-1,12-dicarboxamide, which could be prepared in the same synthetic route as in the preparation of the N,N'-bis(β-D-glucopyranosyl) dodecane-1,12-dicarboxamide excepting replacement of the 2,3,4,6-O-acetyl-β-D-glucopyranosyl bromide with the corresponding L-isomer, i.e. 2,3,4,6-O-acetyl-β-L-glucopyranosyl bromide. The fibrous assemblies thus obtained, having a length of several hundreds of μm, were examined by the use of a phase-contrast light microscope easily to find that each fibrous assembly had an ultrafine fibrous morphology twisted in the direction of a left-hand screw.

EXAMPLE 4

The experimental procedure was substantially the same as in Example 1 excepting replacement of 100 mg of the N,N'-bis(β-D-glucopyranosyl) decane-1,10-dicarboxamide with the same amount (0.16 mmole) of N,N'-bis(β-D-glucopyranosyl) tetradecane-1,14-dicarboxamide, which had been prepared in substantially the same manner as in the Reference Example described above excepting replacement of the 1,10-decane dicarboxylic acid dichloride with the same molar amount of 1,14-tetradecane dicarboxylic acid dichloride, and increase of the volume of water, in which the N,N'-bis(β-D-glucopyranosyl) tetradecane-1,14-dicarboxamide was dissolved, from 7 ml to 20 ml. The fibrous assemblies thus obtained, having a length of several tens to several hundreds of μm, were examined by the use of a polarized-light microscope or phase-contrast microscope easily to find that each fibrous assembly had an ultrafine fibrous morphology twisted in the direction of a right-hand screw.

What is claimed is:

1. A method for the preparation of an ultrafine fibrous assembly having a twisted morphology which comprises the steps of:

(a) dissolving, in water, a glycolipid represented by the general formula

in which G is a residue derived from a D- or L-glucopyranose by excepting the reduced-terminal hydroxyl group and the subscript n is a positive number of 10, 12 or 14, to form an aqueous solution which is heated at a temperature of 90° C. or higher; and (b) cooling the aqueous solution at a rate not exceeding 0.5° C. per minute down to a temperature not higher than 30° C. so as to effect growth of crystallites.

2. The method for the preparation of an ultrafine fibrous assembly having a twisted morphology as claimed in claim 1 in which the cooling rate of the aqueous solution in step (b) does not exceed 0.1° C. per minute.

3. The method for the preparation of an ultrafine fibrous assembly having a twisted morphology as claimed in claim 1 in which the amount of the glycolipid added to water in step (a) is sufficient to give a saturated aqueous solution thereof at a temperature of 90° C. or higher.

* * * * *